(12) United States Patent
Tchouangang

(10) Patent No.: US 7,967,145 B2
(45) Date of Patent: Jun. 28, 2011

(54) KIT FOR FABRICATING AND MAINTAINING DENTURES AND DENTAL APPARATUS AND FOR PERSONAL PROFESSIONAL TOOTH WHITENING BY AUTONOMOUS DENTAL IMPRESSION TAKING

(76) Inventor: Lydie Livolsi Tchouangang, Los Angeles, CA (US)

( * ) Notice: Subject to any disclaimer, the term of this patent is extended or adjusted under 35 U.S.C. 154(b) by 331 days.

(21) Appl. No.: 12/136,922

(22) Filed: Jun. 11, 2008

(65) Prior Publication Data

US 2008/0308450 A1 Dec. 18, 2008

Related U.S. Application Data

(60) Provisional application No. 60/943,605, filed on Jun. 13, 2007.

(51) Int. Cl.
 *B65D 71/00* (2006.01)

(52) U.S. Cl. ................................. 206/570; 206/63.5
(58) Field of Classification Search .................. 206/572
 See application file for complete search history.

(56) References Cited

U.S. PATENT DOCUMENTS

| | | | |
|---|---|---|---|
| 7,048,911 B2 * | 5/2006 | Cashman et al. | 424/49 |
| 7,270,239 B1 * | 9/2007 | Ross | 206/581 |
| 2006/0231453 A1 * | 10/2006 | Grant et al. | 206/570 |
| 2007/0254067 A1 * | 11/2007 | Ha | 426/71 |
| 2008/0011636 A1 * | 1/2008 | St. John et al. | 206/449 |
| 2009/0087393 A1 * | 4/2009 | Jensen et al. | 424/52 |
| 2009/0123217 A1 * | 5/2009 | Ross | 401/134 |
| 2009/0298018 A1 * | 12/2009 | Bublewitz et al. | 433/215 |
| 2009/0325129 A1 * | 12/2009 | Brown et al. | 433/216 |
| 2010/0035211 A1 * | 2/2010 | Monicelli | 433/214 |

* cited by examiner

*Primary Examiner* — Jacob K Ackun, Jr.
(74) *Attorney, Agent, or Firm* — Daniels Patent Law PLLC; Scott A. Daniels

(57) ABSTRACT

The present invention relates to a kit for whitening teeth and a kit for fabricating a dental apparatus and/or denture without visiting the dentist or stomataologist.

5 Claims, 2 Drawing Sheets

KIT FOR FABRICATING AND MAINTAINING DENTURES AND DENTAL APPARATUS AND FOR PERSONAL PROFESSIONAL TOOTH WHITENING BY AUTONOMOUS DENTAL IMPRESSION TAKING

This application claims priority from Provisional Application Ser. No. 60/943,605 filed Jun. 13, 2007.

FIELD OF THE INVENTION

The present invention relates to a kit for whitening teeth and a kit for fabricating a dental apparatus and/or denture without visiting the dentist or stomataologist.

BACKGROUND OF THE INVENTION

At present tooth whitening is accomplished either by using a kit or visiting the dentist. The kit currently available on the market consists of all the items necessary for whitening, including one gutter for the lower jaw and one gutter for the upper jaw; however, the gutters are a standard size and are not customized and made to order. This means that, on the one hand, they are uncomfortable and bothersome for the consumer and on the other hand, because they are not adapted to the unique morphology of each individual, the gel form whitening substance that should normally remain on the tooth enamel spreads throughout the buccal cavity. For this reason the whitening substance has a low concentration (no more than 6%). Under these conditions the results are very unsatisfactory. As a result, consumers return to the dentist for professional tooth whitening using more highly concentrated products.

The dentist or stomataologist will then make individual dental impressions of both jaws. These two impressions will be sent to a prosthetist or assistant who will make a custom size gutter for each jaw. Obviously, a space is provided for each tooth that will receive the gel. Gutters made this way are perfectly stable, and they adapt perfectly to the patient's morphology. They are then sent to the dentist or stomataologist. After explaining their use to the patient, the dentist gives the patient the gutters and the professional whitening product which is in a 22% concentration. The patient applies the professional product to the trays at home, wears them for several hours or overnight, and does this for several days. The results can then be observed.

The present invention also relates to a device for the maintenance and fabrication of custom dentures or dental apparatus without visiting a dentist, using a kit. At present the conventional, simplified fabrication of a dental apparatus is done by a dental prosthetist using dental impressions taken by a dentist that are accompanied by a prescription. In other words, the ultimate purchaser of the dental apparatus never knows the fabricator.

Thus, the dentist or stomataologist takes dental impressions of the patient, tooth, color, occlusion, and sends the information along with a prescription or an order form to his prosthetist, who will fabricate the apparatus and send it to him. He summons his patient and readapts the apparatus and positions it on the patient.

The technique is for the dentist to fill a dental impression of the lower jaw. Various material exist for this purpose, packaged in varying degrees of viscosity (sticks, cartridges for mixing guns, powder, capsules, pots or tubes as indicated).

To take an impression, the dentist or stomataologist dabs the interior of the impression tray with the adhesive recommended for the material he intends to use; this ensures tight adhesion between that material and the impression tray, preventing it from separating when the impression tray is removed from the mouth. The patient is seated alongside in the chair.

The dentist then prepares the impression taking material. For example, for an alginate impression, he mixes powder and water in a bowl that he stirs with a spatula, following the manufacture's recommended mixing time and water/powder ratio. He fills the impression tray with the resulting paste and spreads it uniformly on the edges of the tray. The patient opens his mouth and the dentist diagonally introduces the tray filled with impression taking material. By pivoting it slightly, he moves the handle of the impression tray towards the central axis of the mouth and passes it by the middle of the lips so that the two axes coincide. He separates the lip from the jaw involved with the impression tray and applies digital pressure to push slightly toward the base of the vestibule or the gum so the material flows over the entire jaw. When he feels the base of the gum stopping him, he stops pushing, holds the impression tray in place and waits for the material to harden. When the material is hard (material hardening is ascertained by touching the material that has spread through the perforations in the impression tray), he removes the tray slightly on the side to allow air to enter and then completely removes the impression tray. The impression is thus formed; it is inside the impression tray and will be sent to the prosthetist along with the tray.

Next the dentist takes an impression of occlusion and tooth shade. All of this information and the type of apparatus desired are entered on an order from or a prescription and all are sent to the prosthetist. The dental prosthetist receives the impressions and the prescription. He follows the instructions of the prescriber and fabricates the dental apparatus which he sends to the dentist. The dentist makes the final regulations and adjustments and places the apparatus in the patient's mouth.

OBJECTS AND SUMMARY OF THE INVENTION

The object of the invention is to offer a dental prosthetist or any person who has received adequate instruction, a case or a kit containing everything necessary, that is, the materials and the best suited method, for professionally whitening teeth without visiting the dentist.

The present invention places at the user's disposal a kit containing everything necessary for automatically taking one's own individual dental impressions, including: one lower jaw impression tray; one upper jaw impression tray; impression material; a shade chart; a protective bib; two mixing spatulas; two bowls or mixing material; occlusion wax; a pair of gloves; and instructions for molding one's own dental impressions; two calibrated thermoformable plates and directions for making thermoformed custom gutters; plaster to pour into the trays to obtain working models; spacing product; more highly concentrated professional whitening product with directions for use; mineral toothpaste; and one toothbrush.

The invention eliminates the use of a dentist or stomataologist as an intermediary, thereby considerably reducing cost and delays in fabrication.

The price of professional whitening is lowered because the dental prosthetist has agreed to eliminate the intervention of a dentist or stomataologist.

The present invention also consists of furnishing the dental prosthetist or any person who has received instruction with everything necessary for fabricating and maintaining a dental apparatus in kit form. The kit comprises: items necessary for making one's own molds of both jaws (one upper jaw impression tray, one lower jaw impression tray, impression material with two spatulas and two bowls for mixing compound, one wax strip calibrated for recording occlusion, one protective bib, gloves, a shade chart, and instructions for taking one's individual dental impressions); the operating manual or guide for fabricating dental apparatuses without instructions from the dentist; plaster to make working models and place in the muffle; one plate of photopolymerizable resin; one sheet of calibrated pink wax; and duplicating silicon in order to preserve for several years the impression of the individual's oral morphology at the time the apparatus is made, thus allowing working models to be reproduced as many times as necessary. Thus, if a plaster working model breaks, plaster is poured into this duplicate silicon mold and a working model identical to the first one is produced. Also included is: acrylic dental resin in powder/liquid form or in a block, or other denture making known materials; the fabrication operating manual; plaster-wax insulator; plaster-resin insulator; two cotton swabs for removing the tooth insulator from the apparatus in the muffle; adhesive material for the dental apparatus in paste, pad, or powder form; one toothbrush; one dental apparatus brush; one product for sensitive gums; two tablets or liquid for cleaning dental apparatus; and one cleaning container.

The invention offers the dental prosthetist: the dawn of a new professional opportunity, since the dental prosthetist finally is completely independent of the dentist; the ability to reduce inventory and waste of primary material because of individualized kit packaging (for example, no further need to purchase large tubs of plaster); reduced workspace; reduced cost; freedom of artistic expression, since he can create the model of the apparatus in any way he pleases; and the ability to fabricate devices without metal hooks.

For the consumer, this invention offers: fewer delays in fabrication; lower purchase for dental apparatus due to the elimination of the dentist as intermediary; the opportunity to purchase directly from the manufacturer a more personalized apparatus for esthetic purposes (an actual dental prosthesis), rather than therapeutic purposes as with the dentist; and direct contact with the manufacture.

This invention reduces errors in the transmission of information, since 65% of all dental apparatuses made according to current protocol (office-laboratory-office) have at least one defect. It also allows dental apparatuses to be offered to a wider segment of general public and reduces billing to insurance companies.

The present invention relates to a kit for fabricating a dental apparatus to facilitate the whitening of teeth comprising an upper jaw gutter and a lower jaw gutter a tooth enamel whitening substance where the improvement of the present invention lies in providing a individually formed upper jaw gutter and lower jaw gutter for facilitating the use of a high concentration tooth enamel whiting substance.

The present invention also relates to a kit for fabricating a dental apparatus for whitening teeth further having a lower jaw impression tray, an upper jaw impression jaw tray and impression material.

The present invention relates to a kit for fabricating a dental apparatus for whitening teeth including an inclusion mold and tooth shade comparison chart for determining the patience inclusion tooth shade to obtain the appropriately colored teeth. The improvement further includes gloves and a protective bib.

The present invention also relates to a method for whitening teeth including an upper jaw impression tray, a lower jaw impression tray, an adhesive for spreading each of the lower and upper jaw impression trays mixing a desired impression forming paste on top of the adhesive in both the upper and lower jaw impression trays placing the upper and lower jaw impression trays having the adhesive and impression forming paste into the mouth and making a dental impression of the user's teeth. Fabricating a deformable and resilient copy of the impression so that the impression substantially conforms to the contours and mythology of the user's teeth and gums to facilitate the direct contact of a higher concentration of solution adjacent the users teeth.

DETAILED DESCRIPTION OF THE INVENTION

Figure 1:
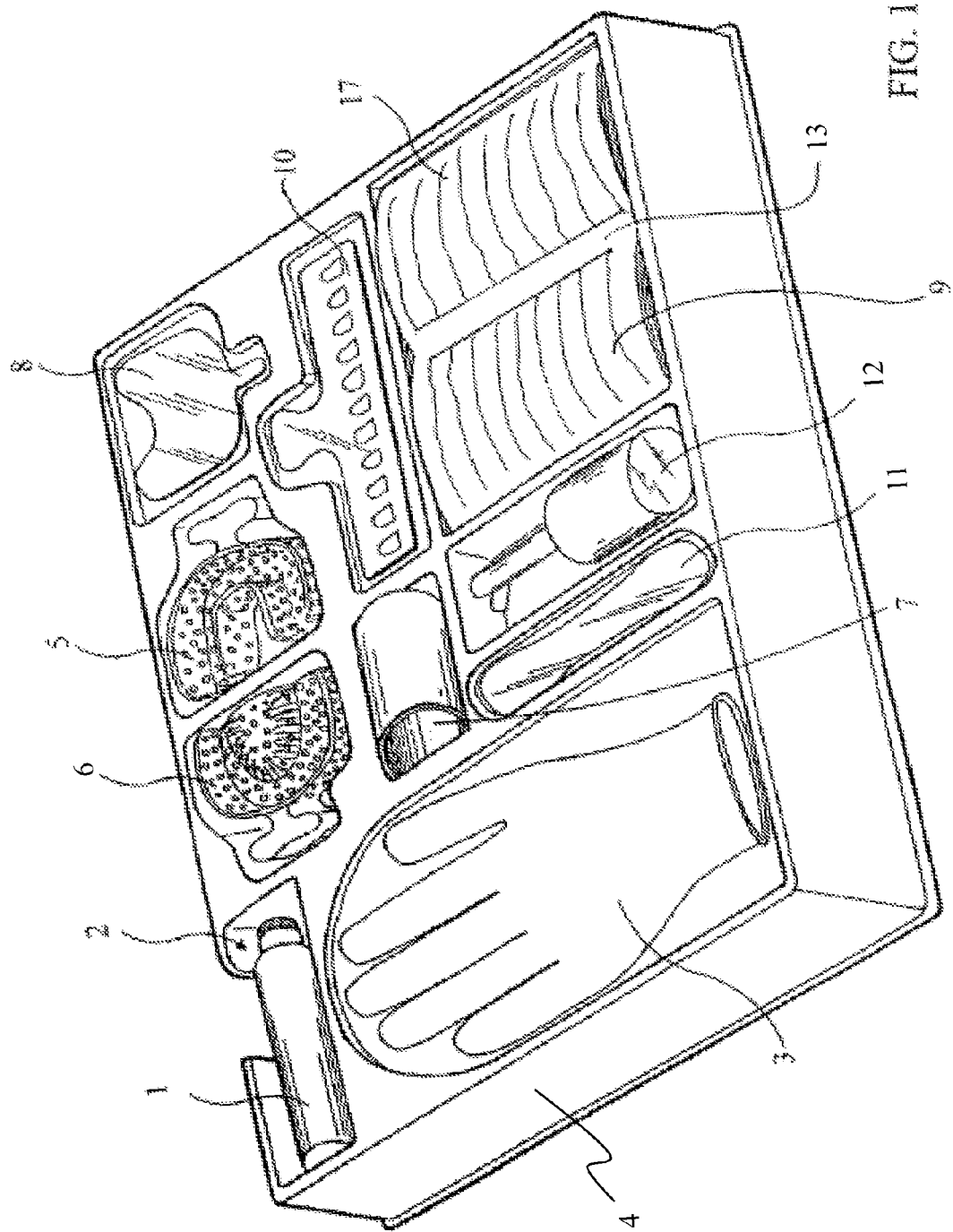
FIG. 1 is a kit for whitening of teeth.

The kit K for the manufacture and maintenance of dentures or individual dental apparatuses or for individual tooth whitening comprises, as shown schematically in FIG. 1, several objects grouped in the same case, package, or box B held by a base that may be made of plastic material which is simple and economical to implement.

Figure 2:
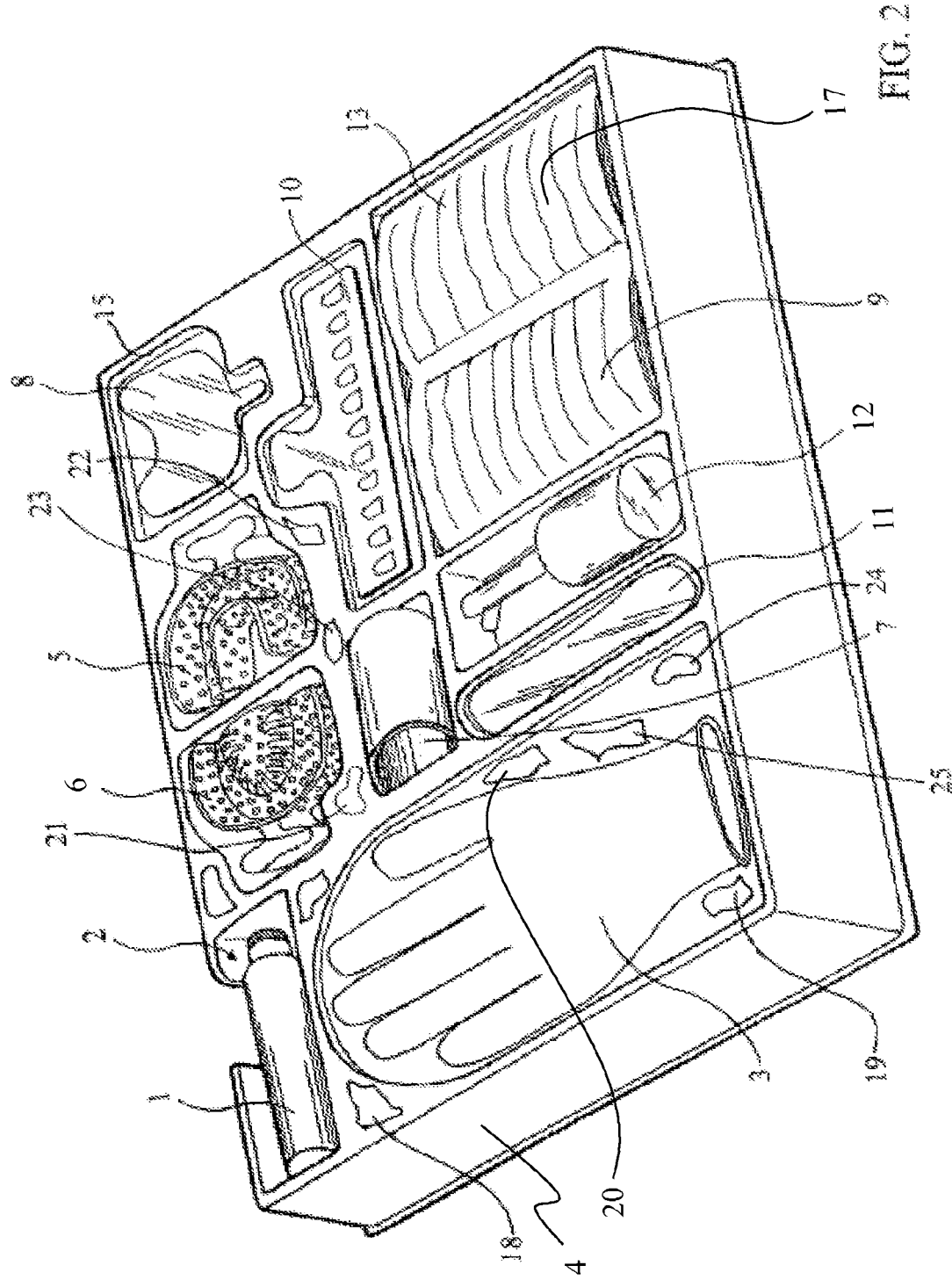
FIG. 2 is a kit for fabrication and maintaining of dentures.

Shown in FIG. 1 is the kit K for individual tooth whitening having:
1 Packet of two-component impression material for the upper jaw
2 Packet of two-component impression material for the lower jaw
3 Gloves and protective bib
4 Compartmented support
5 Lower jaw impression tray pre-impregnated with adhesive
6 Upper law impression tray pre-impregnated with adhesive
7 Mixing bowls
8 Plaster for making working models
9 Instructions for self-molding impressions
10 Shade chart
11 Mixing spatulas
13 Operating manual for fabricating dental apparatuses without visiting the dentist
12 More concentrated professional whitening product
17 Instructions for whitening FIG. 2: A kit for fabricating and maintaining dental apparatuses:
1-13 Same as discussed above in regards to the kit of FIG. 1;
Additional items may include:
Toothbrush
Calibrated heat formable plates
Guide for fabricating gutters
Spacing product
Mineral toothpaste
Strip of occlusion wax
Plaster to put in muffle
One plate of photopolvmerizable resin
One sheet of calibrated pink wax
Duplicating silicon
One container for cleaning dental apparatus.

In order to undertake whitening of the teeth, a dental impression of the individual must be obtained. This occurs by the present invention which relates to individual supplies or a kit for independently taking dental impressions of animals or humans.

The object of the invention is to provide or make available to dentists or any other individuals who are qualified or have been equipped with instructions, a small box or case containing the items best suited for making at least one dental impression or one partial arch or sectional dental impression, or a kit for making an impression for whitening the teeth or resetting or installing dental devices. The invention also concerns taking dental impressions independently.

The invention cuts costs, preparation time, and waste. It occupies less space, reduces product storage, and minimizes the number of products to be sterilized.

The kit for making dental impressions according to the invention offers the following advantages. A dental surgeon, any qualified or experienced person, or simply a person following instructions, can make an impression when needed. The unit is ready to use, in a display unit or package and packed in a convenient kit or a small box constituting a technical commercial unit. Because of this, time is conserved and there is a marked decline in wasted product.

A dentist in a difficult or remote situation, particularly a battlefield, a medical emergency, military base, medical outpost or other temporary arrangements or location far from home, can continue to work effectively.

A veterinarian is provided with a convenient kit that is time-saving and comfortable for the animal.

The invention is also useful for dental surgeons in developing countries who would find purchasing separate units of all the elements required for making dental impressions too expensive relative to the few dental impressions required.

The invention also enables the average person, after suitable education or instruction or a prior demonstration, to satisfactorily make his or her own dental impression.

The invention will be better understood with reference to the following description of one exemplary embodiment with reference to the drawings, wherein the kit for whitening and for taking impressions comprises, as represented schematically in FIG. 1, several objects joined in the same display, case, or box that may take the form of a compartmented support 4 with pockets, indentations, or housings 3. This support may also be made of injected or thermoformed plastic material, for example, a method which allows the housings to be formed easily and which has proven to be simple and economical to use.

The packaging, box, or case can obviously be placed on a display rack. Among the necessary objects and products are first, a material or an impression product 2 for making impressions, packaged in various forms as described below. Next there is at least one impression tray, for example, a universal tray, and if there are two trays, at least one tray 5 for the lower jaw and one tray 6 for the upper jaw for making a full dental arch or demi-arch impression.

The impression tray or each of trays 5 or 6 are preferably adjustable transversely, longitudinally, or in both directions simultaneously, either manually by sliding or deforming parts or by some other means. There may also be rigid, fixed dimension impression trays in a number sufficient to accommodate size differences among individuals.

It is also possible to provide simple impression trays of several sizes. Depending upon the range of sizes to cover, two models may prove insufficient and for this reason it may be necessary to use two or more additional ones if the impression trays have small amplitude of adjustment, or to provide supplementary trays that are children's models.

It is also possible to provide geometrically variable impression trays, for example, trays that adapt by transverse and longitudinal extension.

Also included is a vial 1 or other container of adhesive impression product 2 which will be smeared or pulverized along the internal surfaces of each impression tray at the time it is used, for example, for taking an independent impression. It would also be possible to provide for this purpose an impression tray already coated with adhesive product that would be protected by a sheet or film to be removed at the time of use. Another method may consist of using a product activated at the time of use by some exterior means, for example, a light beam or activating product.

The impression tray or trays also may have been previously impregnated with adhesive product.

The kit also comprises a device for preparing the impression product 2 called the mixer or mixing device which may be in the form of a bowl or a pot 7 and a spatula 6 for working the product 2.

This device may take the form of a mixer-injector with two compartments, for example, in the case of a dual component product, one for the base product and one for the activator or hardener. One exemplary embodiment of this type of mixer-injector is described below.

The kit will also comprise an instrument or a material for recording occlusion such as a sheet of wax 8 or a paste, for example.

The kit will further consist of an instrument or a material for measuring the shade such as for example, a palette or color chart, or other equivalent means 10. For purposes of hygiene, a pair of sterile gloves 3 is included in the package. For use by laypersons, by the subject himself, a family member, or any other person, there are a detailed instructions in the form of a booklet, a pamphlet or several instruction sheets, or audiovisual support, for example, a videocassette, optical disk, or the like.

The mixer-injector device may comprises a body composed principally of two tubular compartments and resting on a base and opening into a mixing chamber where mixing of the two components takes place before they exit from the device through a nozzle or cannula that may be interchangeable. The resulting product may then be easily distributed through the channels or grooves in the bodies of all the impression trays, for example, impression trays 5 and 6. The two components are forced out of tubular compartments and, for example, using a piston system like a syringe with mechanical pushing or pumping action activated by a button or a pushbutton. Thus, the unit could also consist of two juxtaposed syringes, each comprising a piston with their ends connected, manually activated to simultaneously evacuate the two components in the mixing chamber, or any other similar arrangement.

Preferably, the mixer-injector utilizes containers prefilled with micro-doses of product. These containers may be interchangeable and reloaded and changed with each usage. For the variation described above the tubular compartments are filled with measured product at the time of manufacture.

This type of mixer-injector may be a sterile, single-use device, filled with premeasured product when manufactured, or it may comprise interchangeable reloading devices.

This is an original concept since it allows people with missing teeth or with teeth that have lost their whiteness to recover a nice smile thanks to dental wig and/or teeth whitening. The concept is to be found in a shop with a window in which various dental wig are presented, along with gums shields, whitening splints and snoring splints, pictures, products of mouth hygiene and aesthetics.

In the shop one can see many products: a cash-desk, a computer, etc. In order to respect the privacy of customers, there is a small separate room within the shop for autonomous tooth impressions taking, tooth whitening or various fittings. Customers can use a washbasin to wash their hands, brush their teeth. There is also a mirror and a small space for reading small adjustments on the dental wig. But one can also find a coat-hanger, some magazines, a computer corner, the seat for teeth whitening, etc. Also in this room a film on how to take one's dental impressions on one's own is shown around the clock. To put it in a nutshell, this separate room is designed for a more functional service.

By way of example, the potential client enters the shop.

"Hello, can I help you?"

"I would like to know more about what you do."

I immediately direct him/her to the small room called "Salon" and offer him/her a seat.

"Yes, we offer people who have lost a number of teeth to recover their smile. We offer custom made products and sell dental wig."

"What is a dental wig?"

It is a dental wig, like a hairwig, yes wig for teeth (a fashion accessory like shoes for example), without metallic hooks, placed without any intervention from inside your mouth thanks to patented autonomous impression taking procedure, and 100% natural effect. The dental wig is an effective substitute for bridges and implants.

"Without any metallic hooks? That's great! How does it work?"

Take dental wig in your hand and explain: You see, the dental wig has no metallic hook, so it naturally looks nicer. It is designed in such a way that you can press it in like a "lego" block. Moreover the little wings at the ends fit around the gum of adjacent teeth, for better stability and aspect. For extra stability and comfort you can also add a little adhesive paste.

"What is the difference with what dentists do?"

"Dentists are professionals in the domain of health who sell dental prostheses. They would not sell a dental wig." The fundamental difference between dental wig and dental prostheses is first that a wig has no metallic hooks. A metallic hook necessitates an X-ray of support tooth before hand, and thus the dentist's intervention and prescription. Secondly, dental wigs are made from impressions taken by the patients themselves and do not necessitate any prescriptions. For example, a physiotherapist is a professional in the domain of health, who gives medical massages to his patients, whereas a beautician gives non medical massages to her clients. The difference with dental prostheses is that dental wigs are made without a dentist's intervention, that there is no metallic hook and that they can substitute bridges and implants. You can also enjoy a better service at a better price with a shorter wait.

"For a prosthesis for x teeth a dentist will charge you y euros. What about you?"

"Dentists do not make the prostheses they sell. They order them from a prosthodontist and then increases the price by 5, 10 or 15. If for x missing teeth your dentist's quote is inferior or equal to a quote that we have made, this necessarily means that our products and services are just not the same."

"Dentists' prostheses are refunded by Social Security and mutual insurance companies. What about your dental wigs?"

"You know that nowadays insurance companies refund patches for smokers, some yogurt, medical stockings, without any reimbursement by Social Security beforehand. What you have to do is negotiate the refunding of dental wigs with your insurance company. Insurance companies can refund anything, it is just a matter of agreement. Concretely what is your problem?"

"Well I think my teeth are not really white and also I have . . . I don't know how many teeth missing."

Take a cast of the complete mouth and on that cast take out the missing teeth corresponding to the missing teeth in the client's mouth. The operation is done in such a way in order not to put our fingers inside the client's mouth. If we did so, we might be sued for practicing dentistry illegally. Once the disposition of teeth is re-created on the cast, make a sketch of the dental wig on the cast, which helps the client to have an idea of what his dental wig will look like. The cost of the dental wig is estimated.

Than we give the client some explanations:

"You see, if you consider having your teeth whitened, that must be done before making the dental wig. This way you can choose the tooth colour obtained after whitening." Add on the estimation of the costs the estimation concerning the various techniques of whitening. If the client is convinced and decides to order, an invoice is established in his name, which he signs. Once the money is cashed, the work begins.

Autonomous Taking of Impressions of Teeth and of the Mouth Cavity.

While the film is being shown, I explain orally to the client how to proceed. I always stand behind the client who is sitting in front of the mirror. This allows me to observe his every move as I am on the same axis. Usually a dentist sits on the side of their patients, which obliges them to put their fingers inside the mouths of their clients in order to see and feel better.

Ask the client to swallow his saliva and to make as broad a smile as possible. This position allows me to control that the teeth of the two jaws are in contact, without working inside the mouth. Visual control of the contact between the two jaws. Then we determine the colour of the remaining teeth, thanks to a universal palette of colors. Together, we agree on the definitive colour. We also ask him to speak, in order to determine the position of the lips and the general features of the client's face. I wash my hands in the sink.

Using the kit of the present invention, I put the protection bib around the client's neck. I help him put on gloves, and I wear my own gloves. I explain to the client that we will now move on to the practical part (implementation) of the procedure.

I give him an empty impression tray (IT) of the upper jaw and ask him to make the empty IT test: he holds the IT by its handle, introduces it sideways and then brings the handle towards the centre, so that the IT is placed in the middle of the mouth. He then pushes it to the back of his mouth in order to feel that the IT covers all the teeth, including the back teeth. It is important to specify that it is the client's sensation that is fundamental: no one else can feel what he feels better than him. He then covers the front of the IT with his upper lip in order to get a better impression of the whole upper jaw. He places his thumbs under his back teeth and holds this position.

Once the empty IT test is successful, I ask the client to withdraw it and I get it back. The procedure for the lower jaw is the same: give him an empty impression tray of the lower jaw and ask him to make the empty IT test: he holds the IT by its handle, introduces it sideways and then brings the handle towards the centre, so that the IT is placed in the middle of the mouth. He then pushes it to the back of the mouth in order to feel that the IT covers all the teeth, including the back teeth. It is important to specify that it is the client's sensation that is fundamental: no one else can feel what he feels better than him. He then covers the front of the IT with his lower lip in order to get a better impression of the whole lower jaw. He places his forefingers under his back teeth and holds this position. Once the empty IT test is successful, I ask the client to withdraw it and I get it back. Note: when there are no teeth, the client feels the limits of his jaw. Then I tell my client that I am going to prepare the paste for his impressions.

Upper Jaw Impression

I prepare the paste, fill the IT with it and give it to the client, and he takes his own impression by making the same gestures that he made during the empty IT test. Meanwhile, I use the extra paste that I have prepared in order to check the hardening of the paste without putting my fingers inside the client's mouth. Once the paste is hard enough, I ask the client to take out the IT, which I get back. With tissues on which I have sprayed a little sea-water, I clean my client's lips and cheeks, and then proceed to take an impression of the lower jaw.

Lower Jaw Impression

I prepare the paste, fill the IT with it and give it to my client, he takes his own impression by making the same gestures that he made during the empty IT test. Meanwhile, I use the extra paste that I have prepared in order to check the hardening of the paste without putting my fingers inside the client's mouth. Once the paste is hard enough, I ask the client to take off the IT, which I get back. With tissues on which I have sprayed a little sea-water, I clean my client's lips and cheeks, and then proceed to take an impression of the lower jaw. I take his gloves off and give him a tooth-brush with toothpaste on it so that he can brush his teeth. I also offer him a mouth-wash. Once he has finished washing his mouth, I take off his protection bib. We agree on a date for the next session. NOTE: When the client takes an impression of his teeth himself, because it is his own body, the strength he exerts is symmetrically distributed, and therefore the impression thus obtained is more precise than if it had been taken by a third person, a dentist for example.

In the Workshop

Treating the impressions, they are disinfected, decontaminated in a specific solution which eliminates HIV and other germs. I pour liquid plaster into the mould and let it harden in order to obtain a positive cast of the client's jaw. Once the plaster is hard, I remove the cast from the mould and sculpt it with an appropriate tool in order to obtain a neat and exploitable pattern.

On it I spot and mark in pencil: the place of the central fraenum (between the two front teeth); and the place of the median axis between the two canine teeth.

With a soft plastic ruler I measure the distance between the two canine teeth and the distance from the canine to the back of the mouth. With these measures, I choose the size and shape of the teeth that match my client's jaw from the document displaying all sorts of teeth.

I order the teeth and I have chosen in the colour that the client and I chose during our first appointment. Then I make to-measure (in some cases) impression trays and occlusion waxes from the patterns obtained. I use calibrated wax. With wax that is calibrated in height one can be sure to have a maximum height that is close to the real height of teeth, in all cases.

In the Shop, Second Appointment

As for the first appointment, the client makes his own impression with the impression trays I have made. Then I explain to the client what the occlusion wax I have made is for: with missing teeth there is an empty space. Teeth are conceived to remain in contact with adjacent or antagonistic teeth. The presence of teeth secures the balance of the jaws in relation with the articulation of the mouth. Let us note that only the lower jaw moves, while the upper jaw doesn't. That is why I always decide to start by replacing the missing teeth in the upper jaw (that does not move) before those in the lower jaw. As a matter of fact it is easier to adjust the balance of the jaws with the mobile jaw.

Calibrated wax is produced industrially by taking into account the height of false teeth sold in shops. Most of the time, calibrated wax is higher or the same size as the real size we will arrive at after trying it. Consequently, the height will have to be set by diminishing the height of the occlusion wax. Adjustments of the wax consist in maintaining or decreasing the height of the calibrated wax.

It is very rare to have to increase the height of the calibrated wax. In this latter case, it is necessary to use a little moldline paste or silicone paste or sheets of wax that has been calibrated in thickness. To reduce the height, one must heat gently the blade of a cutter which one applies on top of the wax, which melts immediately. The height is controlled regularly until it is correct. The client fully participates in these operations.

Occlusion or the height of teeth is also the making of an impression of the occlusion. We will now proceed to an autonomous making of an impression of the occlusion.

I give my client the occlusion wax I have made to measure and I ask him to try it as we did with the occlusion tray for our previous appointment. He puts it in his mouth and make sure there is no discomfort. If there happens to be feeling of discomfort, the client will show me the precise place with his finger and I will correct the problem on the wax that I hold in my hand. Wax is a material that becomes soft when heated. So we can heat it and give it the shape we want. If the wax is not stable enough, I put in the interior a little quantity of adhesive paste. I then heat the wax, give it to my client who puts it into his mouth, swallows his saliva several times while pressing his teeth hard, the remaining teeth go into the wax which takes their shape. The operation is repeated several times until the client feels that the wax in his mouth is not higher than the other teeth, and particularly than the articulation of the jaw. So when he swallows his saliva and feels no more discomfort, we have reached the correct height, the teeth of the future custom-made dental wig.

While the client makes an impression of the occlusion, I make a visual check of the height of the wax that already materializes the height of the teeth; the volume of the wax in relation to the lips (aesthetic aspect of the lips); the line of the smile; and the middle of the jaw (median axis).

I ask the client to make a little, then a broader smile. With a permanent marker I make the middle of the two central front teeth. I check that this middle fits with the middle of the "M" of the upper lip. The client removes the wax from his mouth, gives it to me and I give him a toothbrush so that he can wash his teeth. He rinses his mouth and we agree on the date of the third appointment.

In Case There is Only One Occlusion Wax

In the case when only one jaw is taken into account. I explain orally to the client what I am going to do: I will soften the upper part of the calibrated wax with a small blowtorch and then the above-mentioned operation will take place. If, while swallowing his salvia, the client tells me that the wax is hard, I ask him to remove it and give it to me and I heat it with a blowtorch. NOTE: If there is to be one wax on each jaw, as said previously, I first deal with the upper jaw and once the dental wig is delivered I start working on the lower jaw dental wig.

It must be said that the mouth is extremely sensitive. We can feel the presence of a hair in our mouth. A dental wig is still a foreign body in the mouth. In order to minimize this sensation, it is always necessary to make one dental wig after the other or else the client feels as though "he had a mountain in his mouth". By starting the fabrication of the lower dental wig after the upper one allows the client to become accustomed to his new dental wig while the second one is being fabricated. As a matter of fact the dental wig needs a few days to find its place in the mouth. Also, this allows us to make final adjustments if necessary.

In the Workshop

I take a basis equipped with a cone; I introduce the female part of the transfer pressure button into the cone and I pour liquid hard plaster into the second impression and I put it back on its base. After the plaster has become hard I obtain a positive cast of hard plaster, I remove it from the mould and sculpt it in order to form a pattern. I am careful to retain as much information as possible in the meantime (fraenum, insertion areas of the ligaments, the back of the vestibule, etc.) Visible on the pattern.

On the plaster cast I draw the future dental wig in pencil. Around each remaining tooth at the end of each toothless segment I draw a wing that will fit around the gum and improve the stability and the aspect of the dental wig. On the palate only, I carve the outline of the dental wig with a big plaster drill in the shape of little wells. In other words, I dig a three-millimeter wide and two millimeter-deep furrow into the plaster to mark the limit of the dental wig. Then I mark the outer limits of the dental wig on the plaster cast with a smaller drill. Digging the outer limits of the dental wig is the best way to make sure that the dental wig will adhere to the plate and that food will not find its way between palate and dental wig.

Making the Silicone Duplicate

I place the pattern thus drawn in a silicone duplication base. I pour into it the liquid silicone mixture and let it become hard as indicated by the manufacture. When it is totally hard, I remove it from the mould and put my pattern away. I fill my silicone mould with a soft plaster paste which I let dry. This silicone duplicate which will be kept during the whole guarantee period allows me have at all times and as many times as possible the pattern from which I have made the initial dental wig.

On my plaster cast, I write the client's name and draw the median axis (the line axis between the two central front teeth of the upper jaw) and the centre of the palate. I prolong this line on the back of the plaster cast. I place the male part of the "transfer pressure button" into its female counterpart. I place the occlusion wax on the cast. I solder it on the cast with liquid hot wax.

Using the Articulator

Using the articulator makes it possible to relocate the various movements of the lower jaw. I place a semi-adaptable or entirely adaptable articulator with its graduated table. I make sure that the settings correspond to the manufacturer's settings. I place the seal on the articulator. I place the articulator on the table as indicated by the manufacturer. I place the wax-soldered group on the plaster cast on the table. I make sure that the cast together with the occlusion wax is not too high so that when I bring down the upper arm of the articulator its shaft comes to rest exactly in the needle. If that is not the case, I use a drill to reshape it.

Visually, I make sure that simultaneously the line that passes by the median axis of the two central front teeth coincides perfectly with, and touches the line of the median axis on the articulator table. Standing in front of the articulator, I close an eye and make sure that the line from the median axis to the center of the palate coincide with the vertical line at the back of the table and that the lateral edges of the occlusion wax coincides systemically with the lateral lines of the table. Then I fix (stabilize) the model-wax block in this position on the table with some hot dental wax. I prepare a soft plaster paste (for the articulation process) which I place on top of the model. I put a thick layer of soft paste in the seal.

When the plaster starts getting hard, I lower the upper arm of the articulator so that its shaft places itself exactly on its needle. I wait while the plaster is getting harder. While it is not yet hard, I remove the excess plaster in order to obtain a pattern with a neat outline. I let it become hard. When it is hard, I remove the table from the group. On the lower arm of the articulator, I place the lower seal. I place my positive cast of the lower jaw on the marks obtained on the wax when my client swallowed his saliva several times at his second appointment while pressing on the wax.

When I have found all the marks, I solder the complete cast of the lower jaw on the occlusion wax, which is soldered on the cast of the upper jaw. I turn the articulator and put it on the worktop. I prepare some more soft plaster paste. I put a good quantity on the lower cast and the lower seal.

I wait until the plaster started getting harder and this is when I bring the upper part down into the lower part. While the plaster is still hardening, I remove the excess plaster in order to obtain a smooth and clean pattern and I let the whole thing become completely hard.

NOTE: While working with the articulator, it is important to make sure that no element has moved. When the plaster is totally hard I separate the pattern of the upper jaw from that of the lower jaw. I remove the occlusion wax from the upper pattern; with a hot steam gun, I clean my two patterns carefully.

Making the Wax Model of the Dental Wig

First I isolate my pattern with a plaster-wax insulating liquid. I then adapt one tooth after the other, the standard teeth which are sold in shops to my client's morphology. I place these adapted teeth on the pattern, one by one. I fix them with hot liquid wax. My adaptable articulator allows me to re-create the movements of my client's jaw at each stage. When all the missing teeth are harmoniously and rigorously placed, using hot liquid wax again, I will reconstitute my client's false gum. Then the wax model is finished. I separate the model and the pattern. I place my model on the pattern again.

Third Appointment

I explain to my client that since the dental wig is custom made he must try the wax model on. I remove the model from the pattern and give it to my client. He places it in his mouth. He swallows his saliva several times while pressing his jaws together. He speaks: generally we start a conversation that will last approximately 20 minutes. In the process the wax and the teeth find their place naturally. Generally no adjustments are needed. I take the wax model, place it on the pattern again and we agree on a date for the fourth appointment.

In the Workshop

I make the wax model and the plaster pattern stick together. Thanks to the "transfer pressure button" I will be able to separate the wax model and the plaster pattern on the one hand, and the seal of the articulator on the other hand (the male part of the transfer pressure button having remained coughed in the quantity of plaster which is on the seal of the upper are of the articulator).

I fill the hole left by the male part of the transfer pressure button with some hot liquid wax. I soak it all in soapy water for a few minutes. In the meantime I rub the part and the counterpart of the muffle with olive oil (olive oil prevents the plaster from adhering to the muffle).

I prepare a sufficient quantity of white plaster cream to fill the part of the muffle. I fill the part of the muffle with plaster in which I dip my pattern which was in soapy water.

I smooth the surface in order to obtain a smooth surface and I let it all become hard. Then I prepare a mixture of self polymerizing resin which I apply to the vestibule side of each tooth in the form of a needle. In this way the plaster of the counterpart will adhere to the tooth in the plaster. With the casting wax shaft, which is 5 millimeters in diameter, I make an injection canal: I place one end of the shaft on the model and the other end is brought to the hole of the injection canal of the muffle. I soak it in soapy water for a few minutes. In the meantime I prepare the plaster cream to all the teeth. I close the muffle with the counterpart and put it all on the vibrator and progressively fill the muffle. I rinse the bowl and the plaster spatula and let the muffle become hard. In the meantime I boil some water.

When the muffle is perfectly hard I plunge the muffle into boiling water and let all the wax melt (it takes approximately 20 minutes). I take the muffle out of the water, I open it, and I flush the surface with clean water then I apply a good quantity of resin plaster and they apply insulating liquid which I apply to the whole surface with a brush and I let the liquid penetrate the plaster deeply.

When the insulating liquid has penetrated and the surface is dry: I take the part of the muffle with teeth and with a medium-sized drill I make retention holes in each resin tooth and I blow some compressed air to clean. I dip a cotton bud into some resin liquid and I wipe the resin teeth in order to rid them of the remaining insulating liquid. I close both parts of the muffle and put it in very hot water. While the muffle is in the hot water I prepare the liquid-resin powder mixture according to the manufacturer's directions.

When the mixture is firm I roll it into a cylinder and I slip it into the injection cylinder. I place the cylinder into its housing in the injection machine. I immediately place the hot cylinder into the injection machine and I put on the flange. I press the pressure injection button. I maintain the muffle under pressure for 5 to 10 minutes. When the water is boiling I remove the flange to the muffle, plunge it into the boiling water and let it boil for one hour. Then I take the muffle out of the water and plunge it into cold water and leave it in until it is completely cold. I open the muffle. I separate the two parts. Delicately I remove the dentarel from the plaster. With a saw I cut the injection needle. I sandblast the dental wig with alumina oxide to remove all the remaining plaster.

Scraping and Polishing of the Dental Wig

I take the silicone duplicate into which I had poured plaster. I remove the duplicate from my patter. I write my client's name on the duplicate pattern. On the silicone mould for duplication I write the client's name, the name of the shop and the month of the order for my archives. As the wax model has been transformed into resin (with the lost wax method) I now use the duplicate to scrape and adjust the dental wig. I scrape the dental wig and adjust it on the duplicate. I polish the dental wig with pumice stone and whiting and it is ready for delivery.

4$^{TH}$ Appointment in the Shop

I put the dental wig back onto the duplicate in front of my client in order to show him how to put it on. I remove the dental wig from the duplicate and give it to my client who puts it into his mouth. We start a discussion, which allows the dental wig to find its place in the mouth. Generally the client is satisfied. I propose the various products necessary to take care of the dental wig. If the client has only ordered an upper dental wig I issue the invoice. If the client has also ordered a lower dental wig:

Making the Lower Dental Wig

Make a self-cast of the upper jaw with its dental wig in place and of the lower jaw and follow the same procedures as for the upper jaw. When measuring the height of the teeth with occlusion wax it is necessary to respect contacts, or the areas of the various contacts between teeth (central incisors, canines, premolar, etc.). This visual check is very important to find the same marks that when using the articulator. It is important to note these figures in the client's records. Follow the same procedure as for making the upper dental wig in 5th, 6th, 7th appointment.

8$^{TH}$ Appointment

Once the client has put the lower dental wig in place in his mouth, give him a paper to check the height of teeth which he places on the teeth then closes his mouth and presses hard. He then takes both dental wig out of his mouth and gives them to me and I remove the excess height. I explain to him how to take care of it and offer to buy the corresponding products. I issue an invoice which is also the starting point of his guarantee.

If the client wishes to have his teeth whitened: We offer him several types of tooth whitening.

Whitening with no-measure splints: from the self-cast of your teeth, we make to measure splints for you. We give you the device and at home you use it according to the manufacturer's directions. Your teeth are white, and they will remain white for 12 to 18 months.

Whitening in one hour in the shop; we apply the whitening product on the enamel of the teeth and we cast a light on it, we repeat the operation three times in one hour. The result is immediate and lasts for 2 to 3 years.

Combined whitening: this system consists in combining both methods. The advantage of combined whitening is that it allows us to whiten all the teeth whereas the one-hour method only applies to the "smile teeth" (from canine to canine).

We also offer splints against teeth-grinding: from a self-cast to your teeth, we make a splint that will stop you from grinding your teeth. We also offer gumshields adapted to all sports.

I claim:

1. A kit for fabricating a dental apparatus by autonomous dental impression taking, the kit comprising an upper jaw impression casting and a lower jaw impression casting for receiving a tooth enamel whitening substance and applying the whitening substance to facilitate the whitening of an individual's teeth, wherein the improvement comprises:
    a malleable upper jaw impression form;
    a separate malleable lower jaw impression form;
    a moldable impression forming material for application into the upper and lower jaw impression forms;
    a tooth shade comparison chart for determining a desired whitening effect to be applied to the individual's teeth;
    a wax strip calibrated for recording occlusion between the upper and lower jaw of the individual;
    a brush and detergent tablets for cleaning the dental apparatus;
    a wax-plaster insulator and a plaster-resin insulator; and
    instructions for molding an individual's dental impressions in the impression forming material using the upper and lower jaw impression forms to enable the fabrication of an upper jaw impression mold and a lower jaw impression mold directly corresponding to the individuals teeth, and from which the upper jaw impression casting and the lower jaw impression casting for receiving a tooth enamel whitening substance is formed.

2. The kit for fabricating a dental apparatus as set forth in claim 1 wherein the kit further includes plaster to make the upper jaw impression casting and the lower jaw impression casting directly corresponding to the individuals teeth.

3. The kit for fabricating a dental apparatus as set forth in claim 2 wherein the kit further includes a desired amount of polymerizable material for application to the upper jaw impression casting and the lower jaw impression casting to create a teeth whitening form directly corresponding to an outer surface of the individuals teeth.

4. The kit for fabricating a dental apparatus as set forth in claim 3 wherein the kit further includes duplicating silicon to fabricate a mold of the upper jaw impression casting and the lower jaw impression casting so as to provide for additional impression castings to be fabricated without the upper and lower jaw impression forms and impression forming material.

5. The kit for fabricating a dental apparatus as set forth in claim 2 wherein the kit further includes an adhesive impregnated in the upper and lower jaw impression trays.

* * * * *